US010766031B2

(12) United States Patent
Shih et al.

(10) Patent No.: US 10,766,031 B2
(45) Date of Patent: Sep. 8, 2020

(54) MICROFLUIDICS BASED ANALYZER AND METHOD FOR FLUID CONTROL THEREOF

(71) Applicant: Feng Chia University, Taichung (TW)

(72) Inventors: Chih-Hsin Shih, Taichung (TW); Ho-Chin Wu, Taichung (TW); Yen-Hao Chen, Taichung (TW)

(73) Assignee: FENG CHIA UNIVERSITY, Taichung (TW)

( * ) Notice: Subject to any disclaimer, the term of this patent is extended or adjusted under 35 U.S.C. 154(b) by 216 days.

(21) Appl. No.: 15/970,866

(22) Filed: May 3, 2018

(65) Prior Publication Data

US 2018/0318836 A1 Nov. 8, 2018

(30) Foreign Application Priority Data

May 5, 2017 (TW) ............................ 106115052 A

(51) Int. Cl.

*B01L 3/00* (2006.01)
*G01N 15/06* (2006.01)
*G01N 33/00* (2006.01)
*G01N 33/48* (2006.01)
*G01N 35/00* (2006.01)

(52) U.S. Cl.

CPC ..... *B01L 3/502738* (2013.01); *B01L 3/50273* (2013.01); *B01L 2200/0621* (2013.01); *B01L 2300/0803* (2013.01); *B01L 2300/0806* (2013.01); *B01L 2300/0864* (2013.01); *B01L 2300/0867* (2013.01);

(Continued)

(58) Field of Classification Search

CPC .......... B01L 3/502738; B01L 3/50273; B01L 2200/0621; B01L 2300/0803; G01N 15/06; G01N 33/00; G01N 33/48; G01N 35/00

See application file for complete search history.

(56) References Cited

U.S. PATENT DOCUMENTS

2005/0084422 A1* 4/2005 Kido ................ B01L 3/502715 422/547
2010/0173394 A1* 7/2010 Colston, Jr. ........... B01F 3/0807 435/287.2

(Continued)

FOREIGN PATENT DOCUMENTS

CN 103566984 A 2/2014
EP 1900432 A2 3/2008

(Continued)

*Primary Examiner* — Brian J. Sines
(74) *Attorney, Agent, or Firm* — Cheng-Ju Chiang

(57) ABSTRACT

The present disclosure relates to a microfluidic-based analyzer, including a drive module and a microfluidic disc. On the microfluidic disk, a capillary is connected between a mixing chamber and a waste chamber. More particularly, the capillary is connected to the mixing chamber through a first access on the first radius of the microfluidic disc, and the capillary is connected to the waste chamber through a second access on the second radius of the microfluidic disk. Specifically, a turn of the capillary is disposed between the first access and the second access, in which a folding is configured on a third radius of the microfluidic disc. Overall, the aforementioned microfluidic-based analyzer is able to be operated in different rotational speeds and is capable of evacuating the mixing chamber and enhancing the washing efficiency.

9 Claims, 17 Drawing Sheets

(52) U.S. Cl.
CPC . *B01L 2400/043* (2013.01); *B01L 2400/0406* (2013.01); *B01L 2400/0409* (2013.01)

(56) References Cited

U.S. PATENT DOCUMENTS

| | | | | |
|---|---|---|---|---|
| 2011/0094600 | A1* | 4/2011 | Bergeron .......... | B01L 3/502738 137/38 |
| 2014/0242721 | A1* | 8/2014 | Kellogg ............... | G01N 33/543 436/501 |

FOREIGN PATENT DOCUMENTS

| | | | |
|---|---|---|---|
| EP | 2952258 | A1 | 12/2015 |
| JP | 2004-309145 | A | 11/2004 |
| JP | 2007-33225 | A | 2/2007 |
| JP | 2010-25645 | A | 2/2010 |
| JP | 2010-122022 | A | 6/2010 |
| JP | 2012-194026 | A | 10/2012 |
| JP | 2014-32171 | A | 2/2014 |
| TW | 200417727 | A | 9/2004 |

* cited by examiner

MICROFLUIDICS BASED ANALYZER AND METHOD FOR FLUID CONTROL THEREOF

TECHNICAL FIELD

At least one embodiment of the present disclosure provides a microfluidics based analyzer and a method for fluid control thereof, more particularly to a microfluidics based analyzer having a microfluidic flow controlling design and an operational method thereof.

DESCRIPTION OF THE RELATED ART

In the conventional analysis methods, the enzyme-linked immunosorbent assay (ELISA) has been widely adopted in medicine, pharmacy, biotechnology, food industry, and environmental testing due to the attributes, such as high specificity, fast, sensitive, low costs, and capable of performing tests simultaneously on a large number of sample.

In the conventional ELISA, the operations are mainly performed on the 96-well microtiters plate. The operations may include an incubation process, a cleaning process, a coloring reaction process, and a detection process. It may take 4 to 6 hours for users to finish all the processes. During each of the processes, the users require to use a large amount of cleaning solution to dilute the residual reagent and drain the reaction chamber after adding the reagent for reaction, so as to reduce detection errors caused by contamination of the reagents in the previous and subsequent steps. For testing a large number of samples, the tedious and highly repeatable steps and actions described above may place a heavy burden on the users and may cause human errors.

To solve the above problem, James Lee et al. proposed the concept of enzyme-linked immunoassay (CD ELISA) on a microfluidic disc platform in early 2000. The CD ELISA may control the processes and steps of ELISA by controlling the rotation speed of the microfluidic disk platform. The users only need to inject the reagents required in each step into each temporary storage chamber on the microfluidic disk, and then select different rotation speeds to release different reagents in sequence, so as to automatically perform the processes, such as the incubation process, the cleaning process, the coloring reaction process, and the detection process of the ELISA. In addition, in the microfluidic system, the reagent volume requirement is small and the surface area of the reaction is large, thus the process of the ELISA may be accelerated. As such, the detection time of the CD ELISA can be shortened within 1 to 2 hours.

However, the CD ELISA has defects. During the step of injecting cleaning solution into the mixing chamber to replace the liquid in the reaction chamber, the cleaning solution may be mixed in the mixing chamber, causing residual reagents in some reaction chambers. Therefore, the cleaning step requires a large volume of cleaning solution and the mixing chamber requires to be rinsed several times to reduce the amount of the remaining reagent and to eliminate the influence resulting from the residual reagents on the detection signals. Moreover, the available space on the microfluidic disc is limited. If the cleaning solution occupies too much space, it may reduce the total number of single-chip inspections and reduce the economic benefits.

Therefore, a microfluidic design capable of improving the cleaning efficiency and reducing the storage space of the cleaning solution is provided. The microfluidic design may increase detection sensitivity, and increase the number of detections on the disc.

SUMMARY

The present disclosure provides a microfluidics based analyzer and a method for fluid control thereof, having a simple operational process and a high cleaning efficiency. Specifically, adopting the microfluidic disc of the present disclosure, the residual liquid in the reaction chamber may be effectively drained, thereby improving the cleaning efficiency and reducing the amount of the cleaning solution. In addition, adopting the method of the liquid flow control through the rotational speed, the reagent may be controlled by the rotational speed, so as to perform an incubation process and a cleaning process. In some examples, the method may only require to control the two stages of the motor, i.e., the high rotational speed and the low rotational speed, to complete all of the inspection steps.

In one aspect, the present disclosure relates to a microfluidic-based analyzer, including: a drive module; a microfluidic disc detachably configured on the drive module, wherein the microfluidic disc includes: at least one injection chamber; at least one microfluidic structure, including: a mixing chamber connecting to the at least one injection chamber; a waste chamber; and a capillary, including: a first access connected to the mixing chamber, wherein the first access is configured on a first radius; a second access connected to the waste chamber, wherein the second access is configured on a second radius; and a turning section connected to the first access and the second access, wherein the turning section is configured on a third radius; wherein the first radius is less than the second radius, and the third radius is less than the first radius.

In another aspect, the present disclosure relates to a microfluidic controlling method of a microfluidic-based analyzer, including: providing the microfluidic-based analyzer described in above; injecting a liquid into the microfluidic structure; operating the drive module at a high rotational speed to control the liquid to flow into the mixing chamber, wherein a rotational speed of the drive module comprises a critical rotational speed, a first rotational speed, and a second rotational speed, the first rotational speed is less than the critical rotational speed, and the second rotational speed is greater than the critical rotational speed; operating the drive module at a low rotational speed, wherein the drive module rotates at the first rotational speed and controls the liquid to flow into the second access by a capillary phenomenon; and operating the drive module at the high rotational speed, wherein the drive module rotates at the second rotational speed, the drive module controls the liquid to penetrate the second access and to enter the waste chamber until the liquid in the mixing chamber is completely drained.

In one example, the rotational speed of the drive module is greater than the critical rotational speed. The drive module only requires a two-stage rotational speed, one is greater than the critical rotational speed of the second access, and the other one is less than the critical rotational speed of the second access.

In one example, the rotational speed of the drive module is switched to selectively retain the agent in the mixing chamber or to drain the agent to the waste chamber.

In one example, adopting the microfluidic disc, the residual liquid in the reaction chamber may be effectively drained, thereby improving the cleaning efficiency and reducing the amount of the cleaning solution. As such, the microfluidic-based analyzer may maintain an accuracy without spending a large amount of the cleaning fluid.

The method for fluid control has a simple operational process. In addition to biochemical testing and medical testing, the method can also be used in areas such as chemical testing, water quality testing, environmental testing, food testing, and defense industries.

DESCRIPTION OF THE PREFERRED EMBODIMENTS

At least one embodiment of the present disclosure provides a microfluidics based analyzer and a method for fluid control thereof, more particularly to a microfluidics-based analyzer having a microfluidic flow control design and an operational method thereof.

Figure 1A:
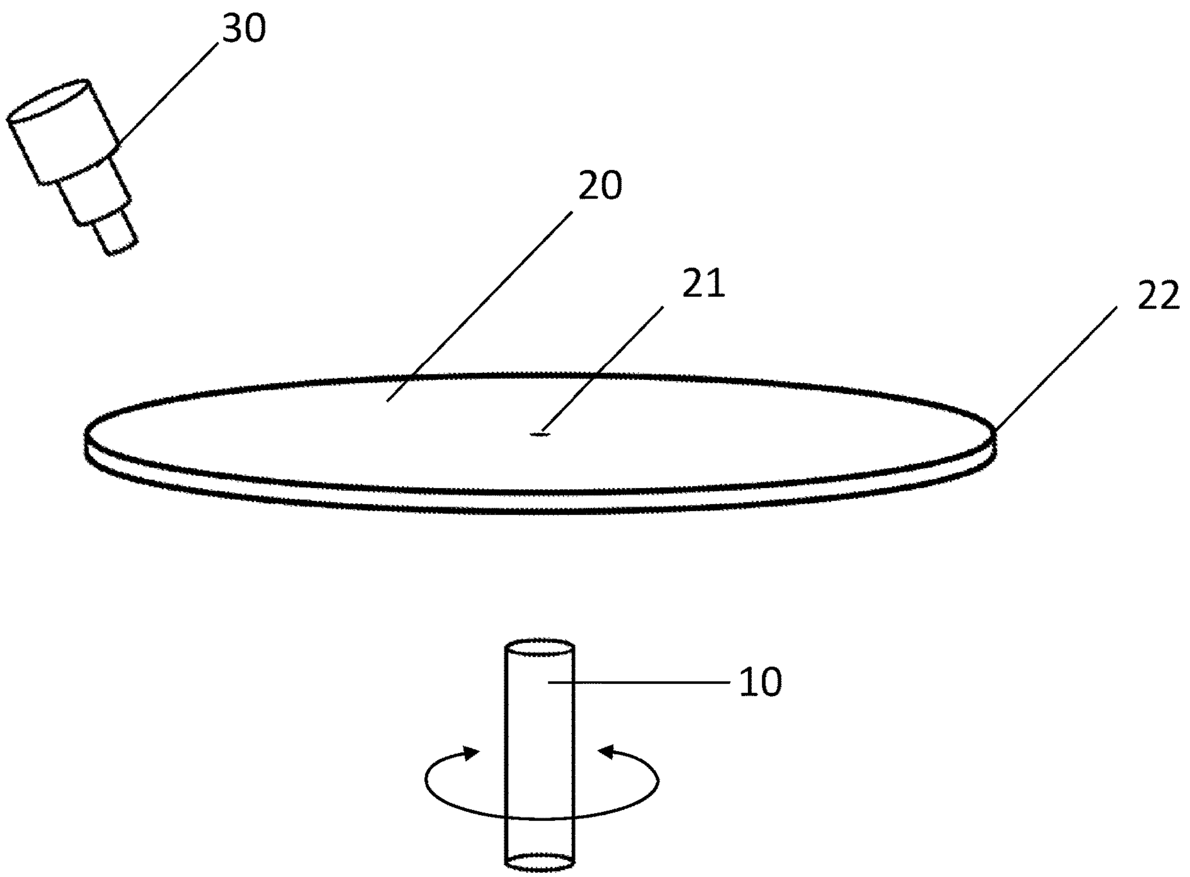
FIG. 1A is a schematic view illustrating a microfluidic-based analyzer in accordance with one embodiment of the present disclosure.
Figure 1B:
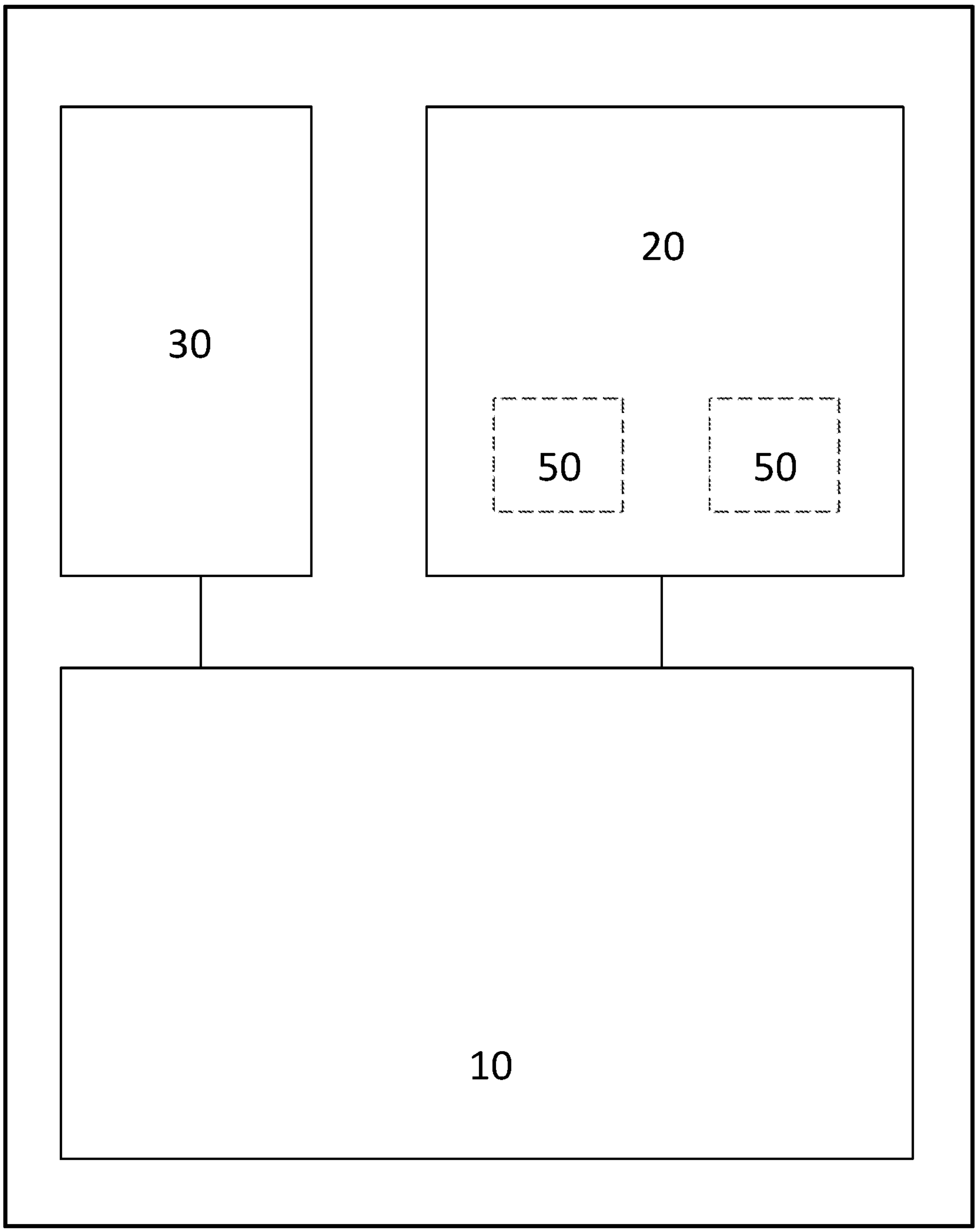
FIG. 1B is a schematic view illustrating a microfluidic-based analyzer in accordance with one embodiment of the present disclosure.

FIG. 1A is a schematic view illustrating a microfluidic-based analyzer in accordance with one embodiment of the present disclosure and FIG. 1B is a schematic view illustrating a microfluidic-based analyzer in accordance with one embodiment of the present disclosure. The microfluidic-based analyzer may include a drive module 10 and a microfluidic disc 20. The drive module 10 is configured to drive and control the microfluidic disc 20 to rotate. The microfluidic disc 20 is detachably configured on the drive module 10. The microfluidic disc 20 has a rotating center 21 and a rim 22. A variety of tests may be conducted on the microfluidic disc 20. As shown in FIG. 1B, the microfluidic disc 20 may include at least one microfluidic structure 50.

In one example, as shown in FIG. 1A, the drive module 10 may be a centrifuge or a rotary motor. When drive module 10 is operating, the microfluidic disc 20 may be controlled to rotate. The microfluidic disc 20 may be a symmetrical disc of circle, square, or polygonal. The microfluidic disc 20 may be made of polyethylene, polyvinyl alcohol, polypropylene, polystyrene, polycarbonate, polymethyl methacrylate, polydimethylsiloxane, silicon dioxide, or a combination thereof.

As shown in FIGS. 1A and 1B, the microfluidic-based analyzer may further include a detector 30. The detector 30 connects to the drive module 10. The drive module 10 is configured to control the microfluidic disc to rotate in accordance with results detected by the microfluidic-based analyzer. For example, the detector 30 may be a spectrophotometer, a colorimeter, a turbidimeter, thermometer, a pH meter, an ohmmeter, a colonometer, an image sensor, or a combination thereof.

Figure 2:
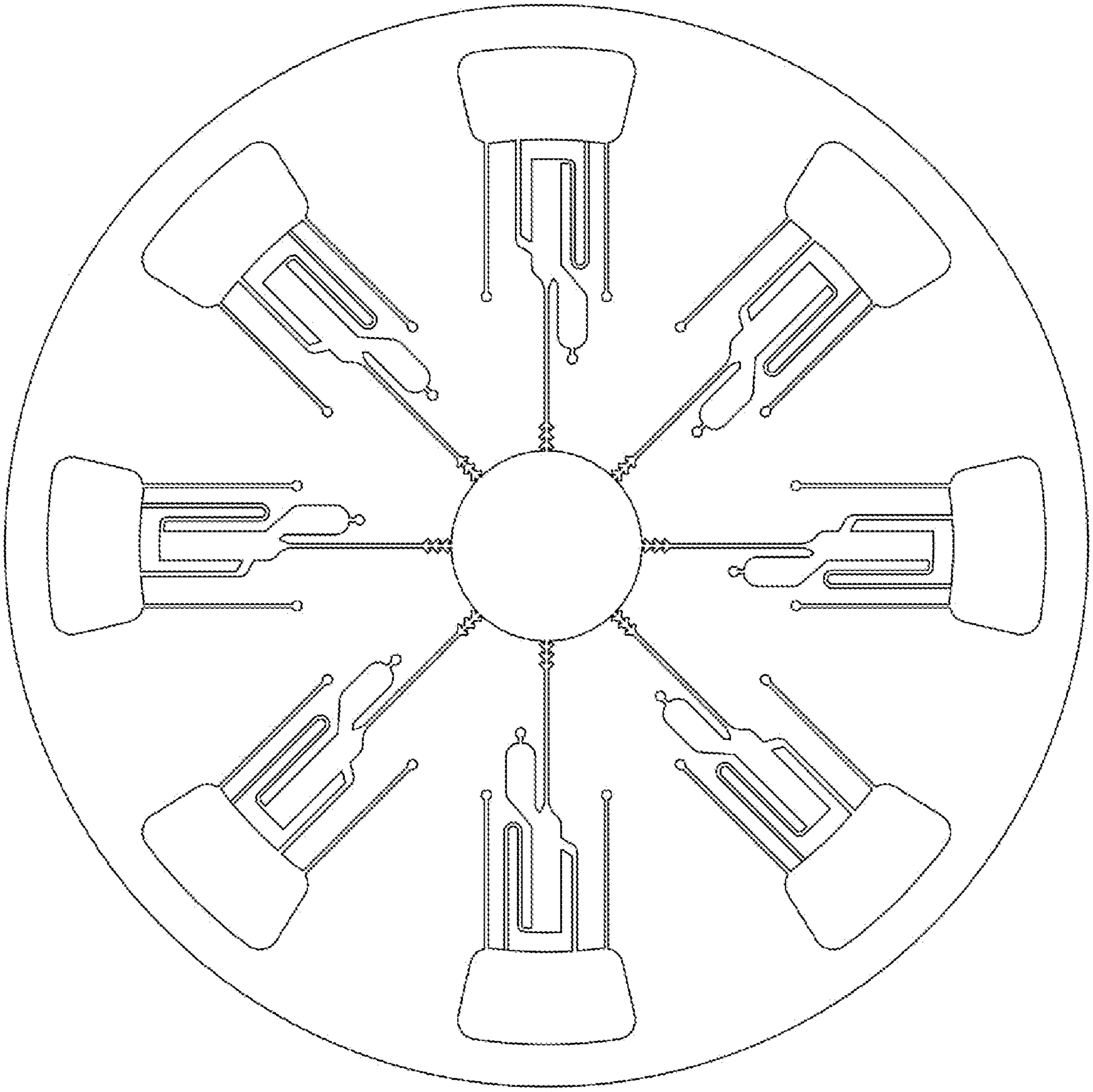
FIG. 2 is a schematic view illustrating a microfluidic disc in accordance with one embodiment of the present disclosure.

Referring to FIG. 2, FIG. 2 is a schematic view illustrating a microfluidic disc in accordance with one embodiment of the present disclosure. The microfluidic disc 20 may include an injection chamber 40 and a plurality of the microfluidic structures 50. The injection chamber 40 is configured on the rotating center of the microfluidic disc 20, and the injection chamber 40 connects to the other elements of the microfluidic structures 50 via individual microfluidic valves 570 of each of the microfluidic structures 50. When liquid is injected into the injection chamber 40, one single liquid may be dispensed into the microfluidic structure 50, and multiple tests may be performed simultaneously. Specifically, after the liquid enters the microfluidic structures 50, the liquid may flow into the microfluidic valve 570, a mixing chamber 520, a capillary 540, and a waste chamber 530 in sequence. The microfluidic structures 50 may include a plurality of ventilation holes 42 configured to reduce resistance resulting from air pressure when the liquid moves in the microfluidic structure 50. For example, the ventilation hole 42 may be configured on a temporary storage 510, the mixing chamber 520, and waste chamber 530. The temporary storage chamber 510 may be arranged according to different detection requirements and is configured to temporarily store other reagents to be injected to the mixing chamber 520. It is noted that not all of the embodiments of the present disclosure require the arrangement of the temporary storage chamber 510. As shown in FIG. 2, a height of the ventilation hole 42 of the waste chamber 530 extending toward the rotating center of the microfluidic disc 20 is higher than a position of an overflow channel 550. That is, the ventilation hole 42 of the waste chamber 530 is closer to the rotating center of the microfluidic disc 20 than the overflow channel 550.

In one example, as shown in FIG. 2, the microfluidic disc 20 may include a plurality of independent microfluidic structures 50. Each of the microfluidic structures 50 connects to one or more of the injection chambers 40. As such, the different liquids may be injected into each of the microfluidic structures 50, and the same test or the different tests may be performed (referring to FIG. 8A to 8G). In another example, the microfluidic structures 50 may be designed as a group. For example, eight of the microfluidic structures 50 on the microfluidic disc 20, which is depending on the requirement, may be designed to be as each two of the microfluidic structures 50 share one injection chamber 40, and each of the injection chambers 40 includes a splitter configured to equally distribute the liquid. The splitter may be of a triangle or a petaloid-shaped. As such, four pairs of the microfluidic structures 50 may be formed on the microfluidic disc 20. When the liquid is injected into one of the injection chambers 40, the liquid may flow through the splitter of the injection chamber 40, and the liquid may be equally distributed. The equally distributed liquid may flow into the two microfluidic structures 50, and two different tests may be performed simultaneously.

As shown in FIG. 2, one kind of the liquid, such as sample, buffer solution, wash buffer, reagent, and solvent, may be injected into the injection chamber 40. In one example, the injected liquid may be magnetic bead solution, which may include at least one magnetic bead, which is in a stationary phase, and solution, which is in a flowing phase. In another example, the injected liquid may be a color development reagent, which may only include the solution which is in the flowing phase.

The microfluidic valve 570 shown in FIG. 2 is configured to prevent the solution from flowing into the mixing chamber 520 in advance at predetermined situations. For example, when the drive module 10, as shown in FIG. 1B, of the microfluidic-based analyzer is operating, the liquid may stay at the microfluidic valve due to confrontation between surface tension and centrifugal force. If the rotational speed of the drive module 10 is increased and the centrifugal force is greater than the surface tension of the liquid, the liquid may flow through the microfluidic valve 570 and flow into the mixing chamber 520.

Figure 3:
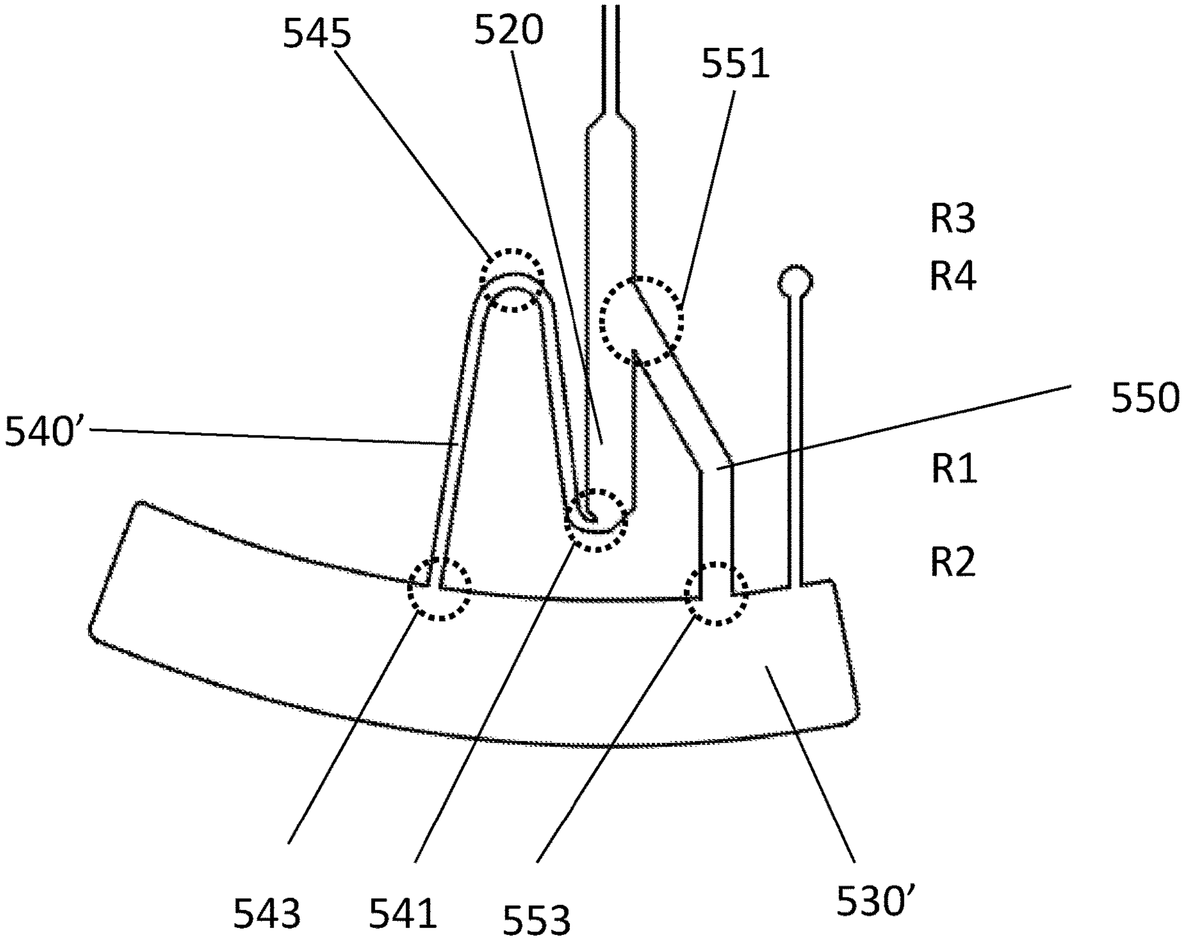
FIG. 3 is a schematic view illustrating a microfluidic structure in accordance with one embodiment of the present disclosure.

FIG. 3 is a schematic view illustrating a microfluidic structure in accordance with one embodiment of the present disclosure. The microfluidic structure 50 shown in FIG. 3 may include the mixing chamber 520, a capillary 540', a waste chamber 530', and the overflow channel 550. A width of the capillary 540' is less than a width of the overflow channel 550. As shown in FIG. 3, the overflow channel 550 is configured to quantify the liquid. A level of liquid surface in the mixing chamber 520 may be controlled by the centrifugal force, and the level of the liquid surface in the capillary 540' and the mixing chamber 520, resulting from a connected tube effect when a gravity force simulated by the centrifugal force is conducted, may be controlled, so as to quantify the liquid.

A connection portion of the capillary 540' and the mixing chamber 520 is configured to be as a first access 541. A connection portion of the capillary 540' and the waste chamber 530' is configured to be as a second access 543. The capillary may include a turning section 545 configured between the first access 541 and the second access 543. A connection portion of the overflow channel 550 and the mixing chamber 520 is configured to be as a third access 551. A connection portion of the overflow channel 550 and the waste chamber 530' is configured to be as a fourth access 553.

The microfluidic structure shown in FIG. 3 is configured on the circular microfluidic disc 20 shown in FIG. 1A. Referring to FIG. 3, a first radius R1, a second radius R2, a third radius R3, and a fourth radius R4 are based on a starting point from the rotating center 21 of the microfluidic disc 20. The first access 541 is configured on the first radius R1. The second access 543 is configured on the second radius R2. The turning section 545 is configured on the third radius R3. The third access 551 is configured on the fourth radius R4. The fourth access 553 is configured on the second radius R2.

A difference between the first radius R1 and the second radius R2 may affect a value of a critical rotational speed $\omega_c$. The critical rotational speed $\omega_c$ is generated by the drive module 10, and is configured to rotate the microfluidic disc 20. The critical rotational speed $\omega_c$ may determine a threshold value of the surface tension that the liquid temporarily stored in the capillary 540' may break before the liquid flows into the waste chamber 530'.

To understand the operational principle of the critical rotational speed $\omega_c$, the detail will be described in below accompanying with FIG. 4, FIG. 5, and FIG. 6A to FIG. 6F.

Figure 4:
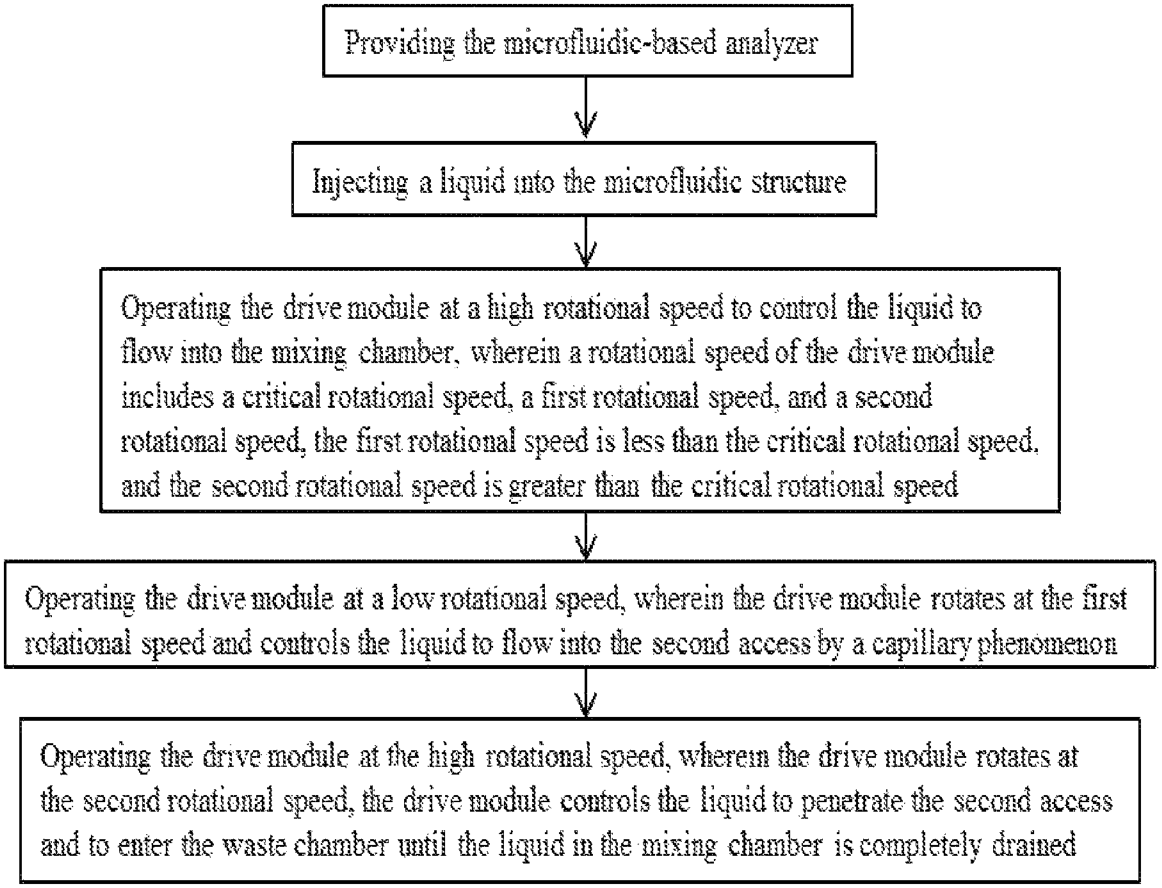
FIG. 4 is a flowchart illustrating a method of operating a microfluidic-based analyzer in accordance with one embodiment of the present disclosure.

FIG. 4 is a flowchart illustrating a method of operating a microfluidic-based analyzer in accordance with one embodiment of the present disclosure. The method includes: providing the microfluidic-based analyzer shown in FIG. 2; injecting the liquid into the microfluidic structure, operating the drive module at a high rotational speed to control the liquid to flow into the mixing chamber, wherein a rotational speed of the drive module includes a critical rotational speed $\omega_c$, a first rotational speed, and a second rotational speed, the first rotational speed is less than the critical rotational speed $\omega_c$, and the second rotational speed is greater than the critical rotational speed $\omega_c$; operating the drive module at a low rotational speed, wherein the drive module rotates at the first rotational speed and controls the liquid to flow into the second access by a capillary phenomenon; and operating the drive module at the high rotational speed, wherein the drive module rotates at the second rotational speed, and drive module controls the liquid to flow through the second access and to enter the waste chamber until the liquid in the mixing chamber is completely drained.

In one example, the second rotational speed may include a plurality of driving rotation speeds. The driving rotation speeds are all greater than the critical rotational speed $\omega_c$ shown in FIG. 8A to FIG. 8G. Similarly, the first rotation speed may arbitrarily be changed according to the embodiment and detection content, and the present disclosure is not limited thereto.

Figure 5:
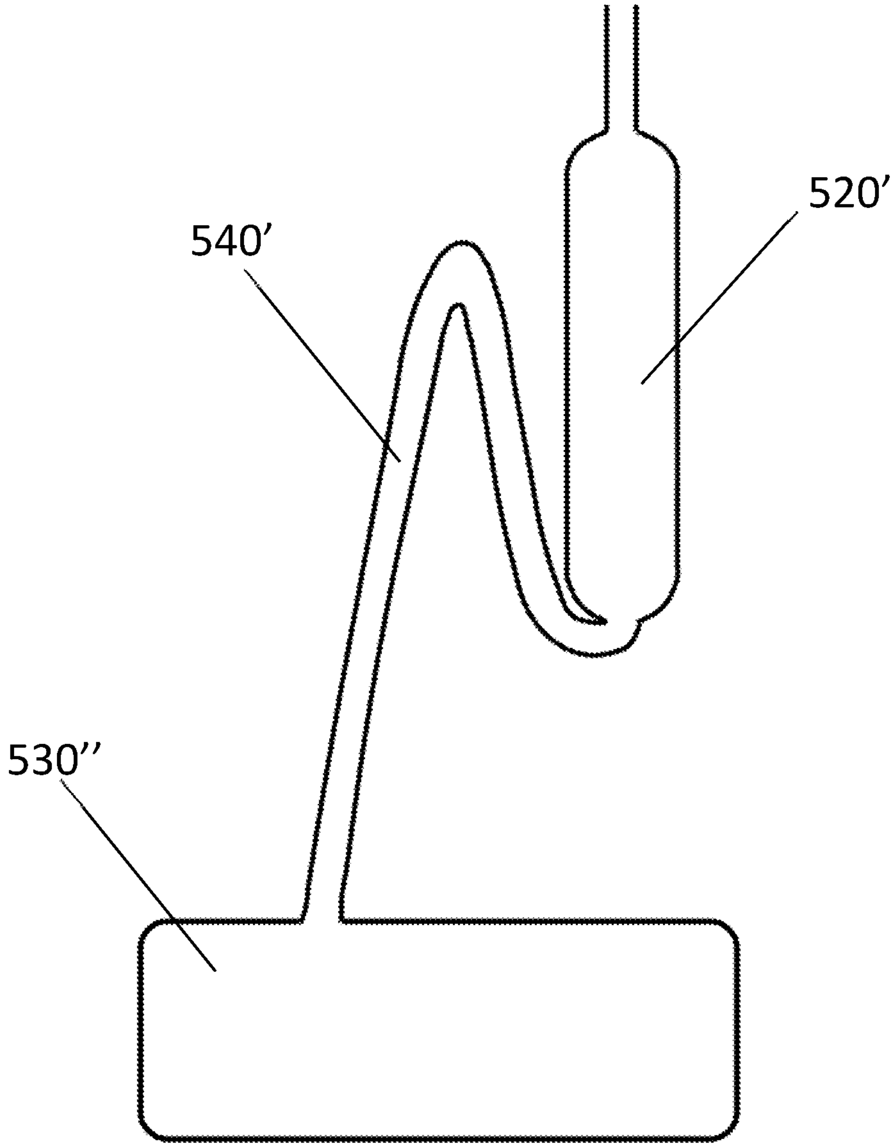
FIG. 5 is a schematic view illustrating a microfluidic structure in accordance with one embodiment of the present disclosure.

Referring to FIG. 5, FIG. 5 is a schematic view illustrating a microfluidic structure in accordance with one embodiment of the present disclosure. The microfluidic structure may include a mixing chamber 520', the capillary 540', and a waste chamber 530". Two ends of the capillary 540' respectively connect to the mixing chamber 520' and the waste chamber 530". FIG. 5 illustrates a portion of the microfluidic structure shown in FIG. 1B. Configuration of the mixing chamber 520', the capillary 540', and the waste chamber 530" is similar to configuration of the mixing chamber 520, the capillary 540, and the waste chamber 530' shown on FIG. 3. In addition, the mixing chamber 520 shown in FIG. 5 may further connect to other elements of the microfluidic disc 20.

Figure 6A:
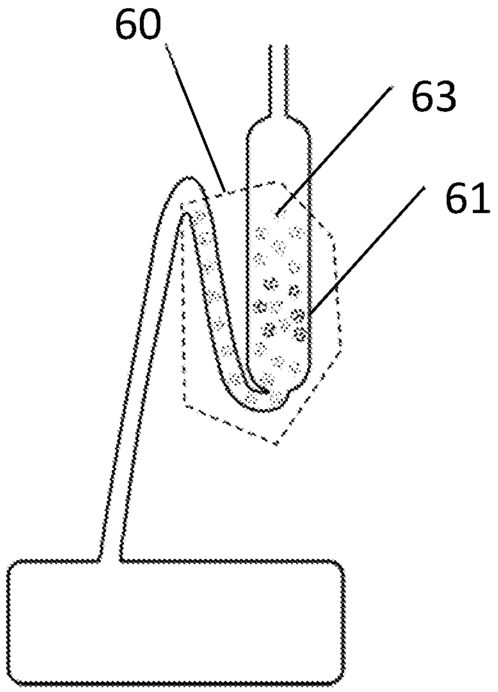
FIG. 6A to FIG. 6F are diagrams illustrating a method of operating a microfluidic-based analyzer in accordance with one embodiment of the present disclosure.

FIG. 6A to FIG. 6F are diagrams illustrating a method of operating a microfluidic-based analyzer in accordance with one embodiment of the present disclosure. FIG. 6A to FIG. 6F illustrate operational process of the microfluidic structure, and motions and distribution of the liquid inside the microfluidic structure. When first liquid 60 is injected into the microstructure shown in FIG. 5 by a high centrifugal force, the distribution of the liquid is shown in FIG. 6A. Comparing the structures shown in FIG. 6A and FIG. 3, it can be seen that both of the structures include the capillary 540', the turning section 545, the first radius R1, and the second radius R2. The differences between the structures shown in FIG. 6A and FIG. 3 reside in that the structure shown in FIG. 3 includes the overflow channel 550. For the experiments that have been conducted by a liquid quantification process, the overflow channel 550 is a selective structure configured to cooperate with the injection chamber and the centrifugal force.

In one example, as shown in FIG. 6A, the first liquid 60 may include the stationary phase 61 and the flowing phase 63. The stationary phase may be magnetic beads, and the flowing phase may be the solution. The flowing phase 63 in the mixing chamber 520' and the capillary 540' may have the same level due to the connected tube effect resulted from the gravity force simulated by the centrifugal force. The turning section 545 of the capillary 540' configured on the third radius R3 is configured to form the connected tube effect.

Figure 6B:
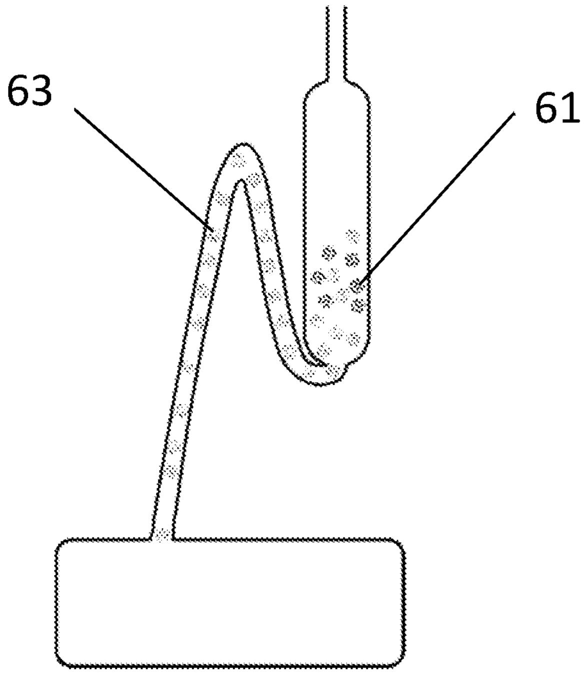

As shown in FIG. 6B, when the drive module decelerates the rotational speed, the centrifugal force may be reduced, and the flowing phase 63 of the first liquid 60 may flow into and fill up with the capillary 540' due to the capillary phenomenon. That is, a capillary force is greater than the gravity force simulated by the centrifugal force. The first liquid 60 may stay at an intersection between the capillary 540' and the waste chamber 530' due to the surface tension, i.e., the first liquid 60 may stay at a position of the second access 543 shown in FIG. 3.

Figure 6C:
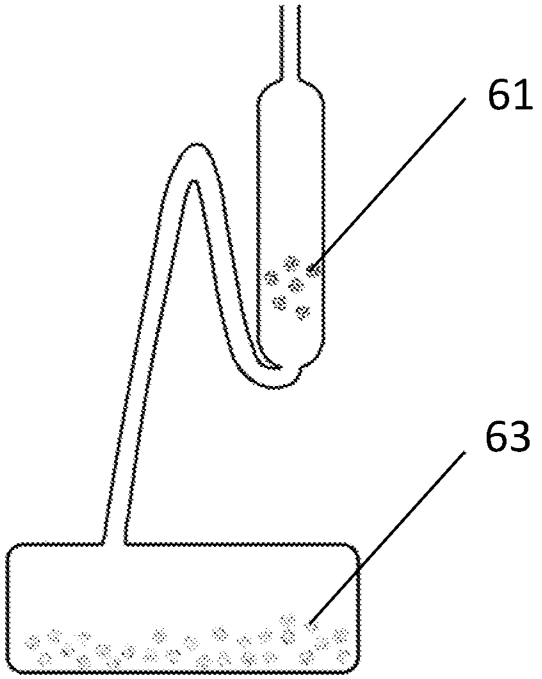

Referring to FIG. 6C, the drive module accelerates the rotational speed again to break the surface tension at the second access 543 by the centrifugal force. The flowing phase 63 in the capillary 540' may flow into the waste chamber 530". The centrifugal force of the flowing phase 63 at the second access 543 shown in FIG. 3 may be obtained by the formula below.

$$\Delta P_c = \rho\omega^2 \Delta R \bar{R} \quad (1)$$

The centrifugal force of the flowing phase 63, which is configured to break the surface tension at the second access 543 and is obtained by the formula above, is the centrifugal force that must be capable of breaking the surface tension. In other words, not all embodiments require such great centrifugal force to break the surface tension.

In the formula (1), "ρ" indicates a liquid density of the flowing phase 63. "ω" indicates the rotational speed. "ΔR" indicates a height difference of the first radius R1 and the second radius R2. "$\bar{R}$" indicates an average radius of the capillary 540'. "ΔR" is defined as the height difference of the first radius R1 and the second radius R2 due to the gravity force is simulated by the centrifugal force. In one example, the height difference indicates a radius difference between the first radius R1 and the second radius R2 based on the starting point from the rotating center of the microfluidic disc 20.

Therefore, when the flowing phase 63 in the capillary 540' breaks the surface tension and flows into the waste chamber 530" by the gravity force simulated by the centrifugal force, the flowing phase 63 in the mixing chamber 520' may be controlled to flow into the waste chamber 530" continuously until the first liquid 63 in the mixing chamber 520' and the capillary 540' is completely drained to the waste chamber 530" by a stress, such as a siphon effect.

A pressure difference of the surface tension of the flowing phase 63 may be obtained by the formula below.

$$\Delta P_s = \frac{C\gamma \sin\theta}{A} \quad (2)$$

In formula (2), "C" indicates a surface tension constant which may be adjusted according to different flowing phases 63. "γ" indicates the surface tension. "θ" indicates a contact angle of the flowing phase resulting from the liquid surface bended by the surface tension at the second access 543. "A" indicates a cross-sectional area of the second access 543. Therefore, according to the formula (1) and formula (2), a formula of the critical rotational speed $\omega_c$ may be obtained by the formula as below.

$$\omega_c = 60\left(\frac{\gamma \sin\theta}{\pi^2 d_H \rho \Delta R \bar{R}}\right)^{0.5} \quad (3)$$

In formula (3), "$d_H$" may change according to a height and a width of the second access 543, and "$d_H$" may be obtained by the formula below.

$$d_H = \frac{2WH}{(W+H)} \quad (4)$$

In formula (4), "W" indicates the width of the second access 543. "H" indicates the height, which is a parameter to form an interface of liquid and gas.

Figure 6D:
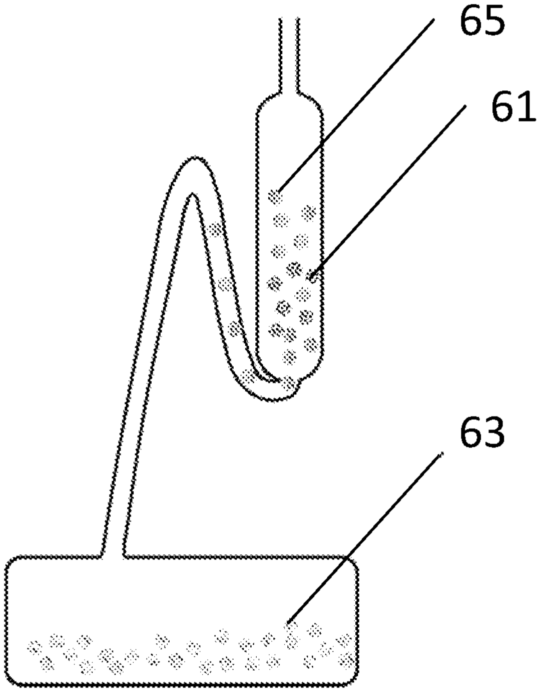
Figure 6E:
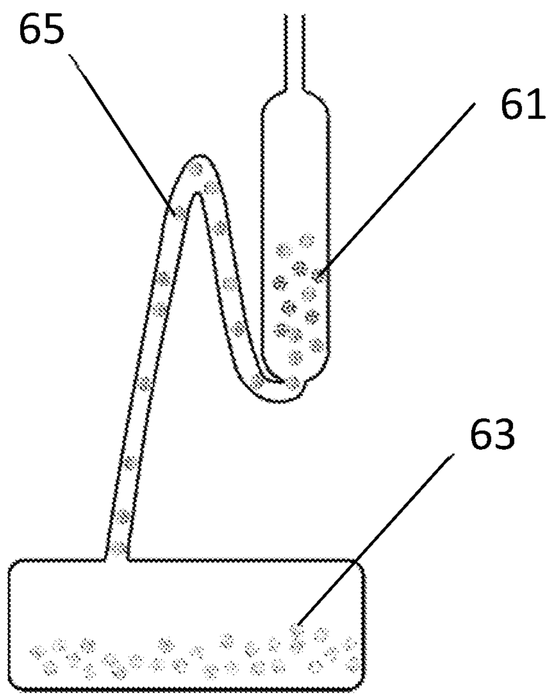

As shown in FIG. 6D, a second liquid 65 is injected into the mixing chamber 520'. Similar to the first liquid 60, the second liquid 65 in the mixing chamber 520' and the capillary 540 may have the same level when being conducted by the high centrifugal force. As shown in FIG. 6E, when the drive module decelerates the rotational speed, the centrifugal force may be reduced, and the second liquid 65 may flow into and fill up with the capillary 540'. The second liquid 65 may stay at the second access due to the surface tension.

Figure 6F:
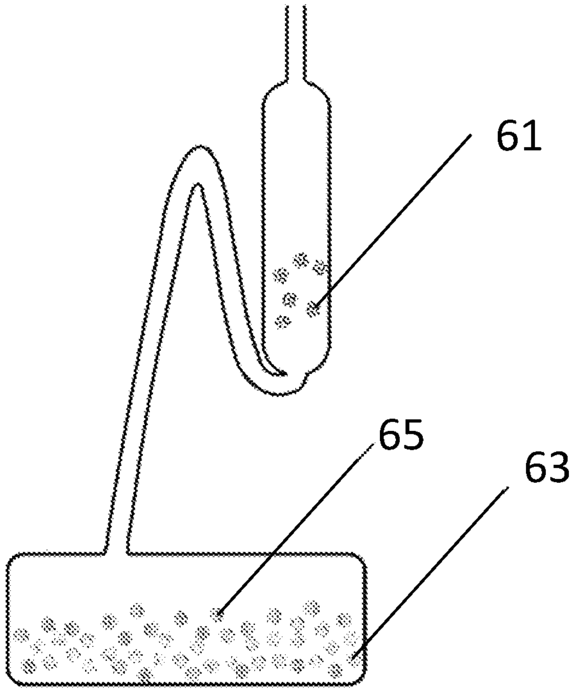

As shown in FIG. 6F, when the drive module accelerates the rotational speed again, the surface tension at the second access may be broken by the high centrifugal force, and the second liquid 65 in the capillary 540' may flow into the waste chamber 530". The second liquid 65 in the mixing chamber 520' may continuously be drained to the waste chamber 530" by the syphon effect until the second liquid 65 in the mixing chamber 520' and the capillary 540' is completely empty. In the above process, the stationary phase 61 may be retained in the mixing chamber 520' by an external force.

The rotational speed of the drive module 10 shown in FIG. 6C and FIG. 6F is greater than the critical rotational speed $\omega_c$. Such that the flowing phase 63 may break the surface tension and flow into the waste chamber 530". In one example, a wall of the capillary 540' may be made of polymethyl methacrylate (PMMA) and an oxygen plasma may be conducted on a portion of the PMMA to perform a surface hydrophilic treatment.

Figure 7:
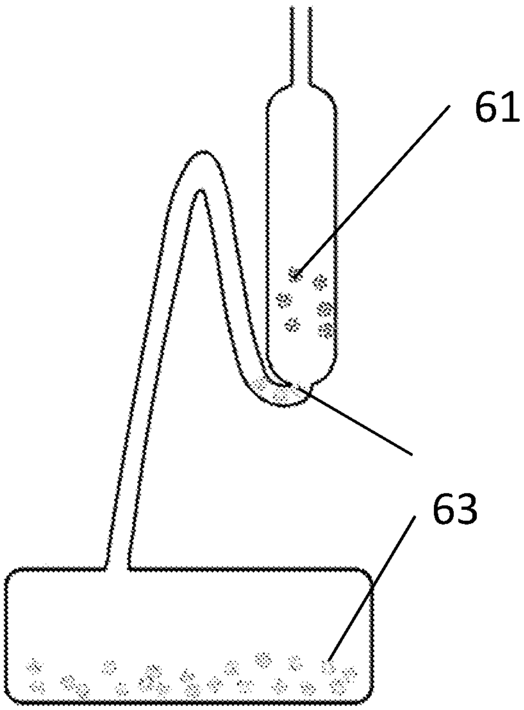
FIG. 7 is a diagram illustrating a method of operating a microfluidic-based analyzer in accordance with one embodiment of the present disclosure.

FIG. 7 is a diagram illustrating a method of operating a microfluidic-based analyzer in accordance with one embodiment of the present disclosure. The microfluidic structures shown in FIG. 6C and FIG. 7 are similar. The difference between the microfluidic structures shown in FIG. 6C and FIG. 7 resides in that the rotational speed of the drive module shown in FIG. 7 is less than the critical rotational speed ω. As shown in FIG. 7, the rotational speed of the drive module is less than the critical rotational speed ω, and the pressure difference resulting from the centrifugal force is too small to completely drain the flowing phase 63 in the mixing chamber 520'. Thus, the flowing phase 63 may fill up with the capillary 540 due to the capillary phenomenon. After the second liquid 63 flows into the mixing chamber 520' in the following steps, the second liquid 65 may be drained to the waste chamber 530" since the second liquid 65 is in contact with the flowing phase 63, and the second liquid 65 may not be retained in the mixing chamber 520'.

At least one embodiment of the present disclosure adopts the microfluidic-based analyzer shown in FIG. 1A to cooperate with the microfluidic disc shown in FIG. 2 to perform the enzyme-linked immunosorbent assay (ELISA). First, 1 μl of the magnetic bead solution, 10 μl of detection antibody, and 20 μl of antigen are injected into the mixing chamber 520 of the microfluidic disc 20. The microfluidic disc 20 is configured on the drive module 10, and the drive module 10 is activated to accelerate the rotational speed to 4000 revolutions per minute (RPM). When the magnetic bead solution, the detection antibody, and the antigen are mixed to form the first liquid, the drive module may decelerate the rotational speed to 10 RPM and maintain the rotational speed for 30 minutes. As such, the magnetic bead solution, the detection antibody, and the antigen may fully react and form a bond. Due to the centrifugal force is not enough to simulate the gravity force and inhibit the capillary phenomenon, the flowing phase of the first liquid may flow into the capillary 540 by the capillary force. After the reaction is completed, the drive module 10 may accelerate the rotational speed to 4000 RPM again. At the high rotational speeds, which are continuously maintained without interruption, the flowing phase in the mixing chamber 520 may be drained to the waste chamber 530 due to the pressure difference resulting from the gravity force simulated by the centrifugal force, and only the stationary phase, such as the magnetic beads, may stay in the mixing chamber 520. When it is determined that the flowing phase in the mixing chamber 520 is completely drained, 320 μl of the wash buffer may be injected into the injection chamber 40, and the drive module 10 may be activated again to accelerate the rotational speed to 4000 RPM. In this step, injecting the wash buffer after determining the flowing phase in the mixing chamber 520 is completely drained is to prevent the wash buffer from contacting with the flowing phase and being drained to the waste chamber 530 before the mixing chamber is cleaned. The wash buffer may be distributed to each of the mixing chamber 520 from each of the microfluidic structures. After the wash buffer has been distributed, the drive module 10 decelerates the rotational speed to 10 RPM to clean the stationary phase in the mixing chamber 520. A portion of the wash buffer may flow into the capillary 540 due to the centrifugal force is not enough to inhibit the capillary phenomenon.

After cleaning the stationary phase in the mixing chamber 520, the drive module 10 may accelerate the rotational speed again to 4000 RPM. The wash buffer in the mixing chamber 520 may be controlled to drain to the waste chamber 530 by the pressure difference resulting from the centrifugal force, and only the stationary phase, such as the magnetic beans, may stay in the mixing chamber 520. Then, 48 μl of the color development reagent may be injected into the injection chamber 520, and the drive module 10 may be activated to accelerate the rotational speed to 4000 RPM. In this step, the color development reagent may be distributed to each of the mixing chamber 520 from each of the microfluidic structure 50. After the color development reagent is distributed, the drive module 10 decelerates the rotational speed to 10 RPM and maintains the rotational speed for 15 minutes. As such, the color development reagent may fully react with the stationary phase in the mixing chamber 520. Reaction results may be detected after the coloring process is completed.

Figure 8A:
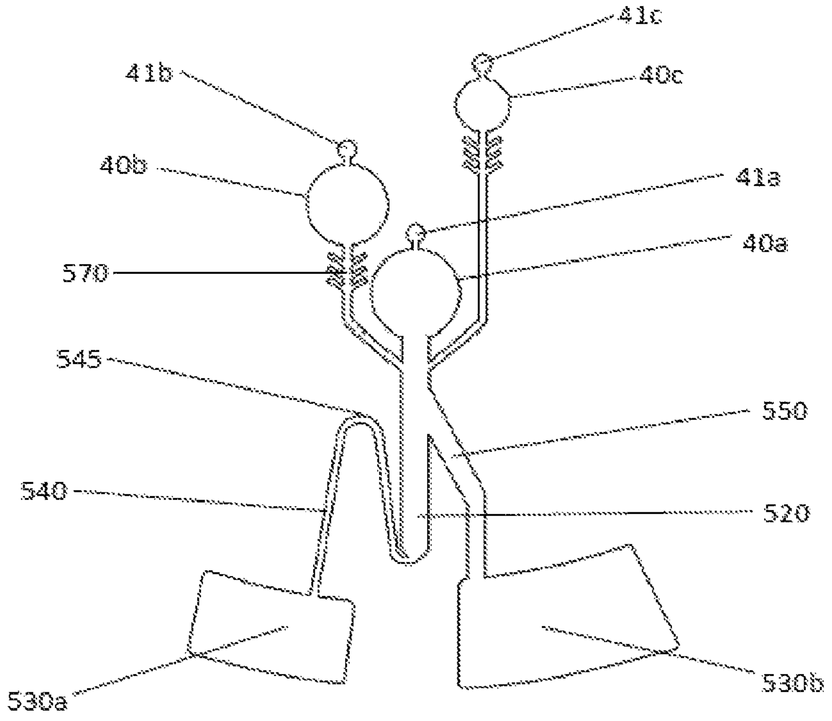
FIG. 8A to FIG. 8G are diagrams illustrating a method of operating a microfluidic-based analyzer in accordance with another embodiment of the present disclosure.

Referring to FIG. 8A to FIG. 8G, FIG. 8A to FIG. 8G are diagrams illustrating a method of operating a microfluidic-based analyzer in accordance with another embodiment of the present disclosure. In one example, the test described in the present disclosure may adopt an enzyme-linked immune sorbent assay. As shown in FIG. 8A, the mixing chamber 520 in configured to connect to three injection chambers 40*a*, 40*b*, and 40*c*. The injection chamber 40*b* and the injection chamber 40*c* respectively connect to the mixing chamber 520 via the arrow-shaped microfluidic valves 570. In one example, the injection chambers 40*a*, 40*b*, and 40*c* may respectively include an injection hole 41*a*, 41*b*, and 41*c* in sequence. In another example, the microfluidic valve 570 may be of spherical or beaded-shaped, and the present disclosure is not limited thereto.

Figure 8B:
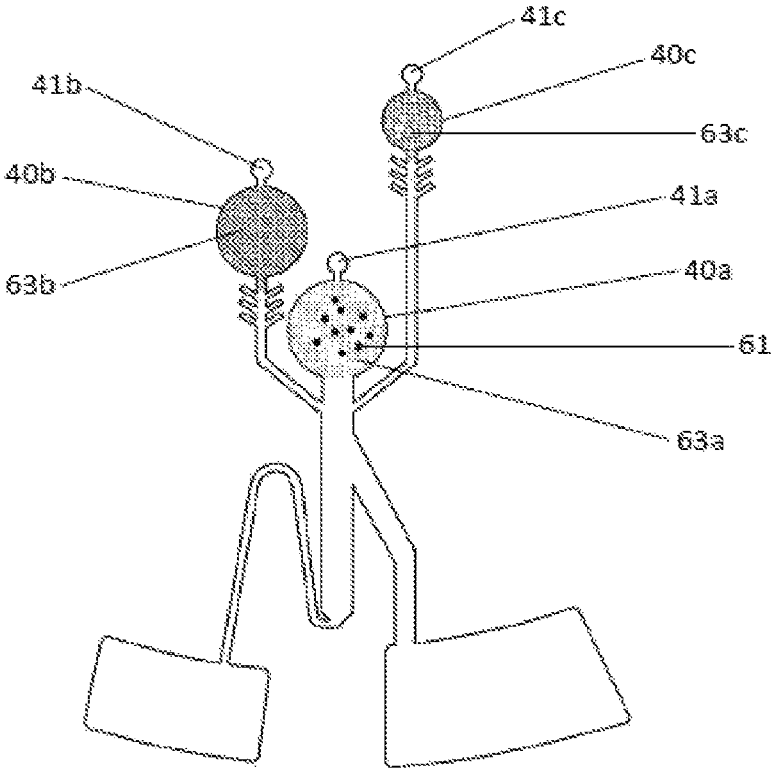
Figure 8C:
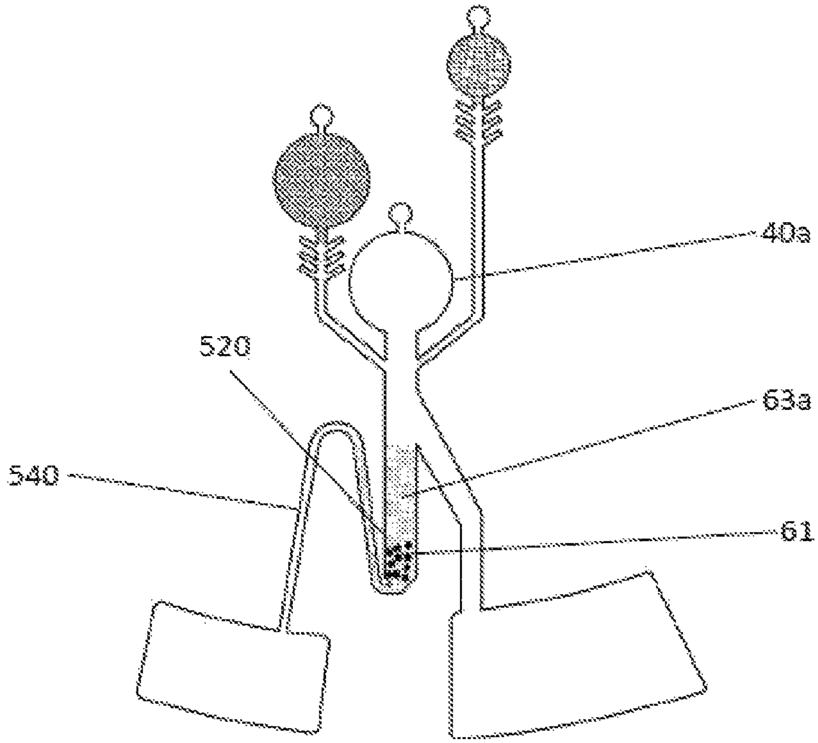

As shown in FIG. 8B, the stationary phase 61 and a flowing phase 63*a* are injected into the injection hole 41*a*. In one example, the stationary phase 61 may be 1 μl of the magnetic bead having a surface with capture antibodies, and the flowing phase 63*a* may be a solution of 10 μl of the detection antibodies and 20 μl of the antigens. A flowing phase 63*b* and a flowing phase 63*c* are injected into the injection holes 41*b* and 41*c* in sequence. For example, the flowing phase 63*b* may be 40 μl of the wash buffer, and the flowing phase 63*c* may be 10 μl of the color development reagent.

In one example, the critical rotational speed w may be 850 RPM. After the microfluidic disc 20 is configured on the drive module 10 and the drive module 10 is activated to accelerate to the second rotational speed, i.e., 1000 RPM, the connected tube effect may be generated on the flowing phase 63*a* due to the gravity force simulated by the centrifugal force causing by the second rotational speed.

Figure 8D:
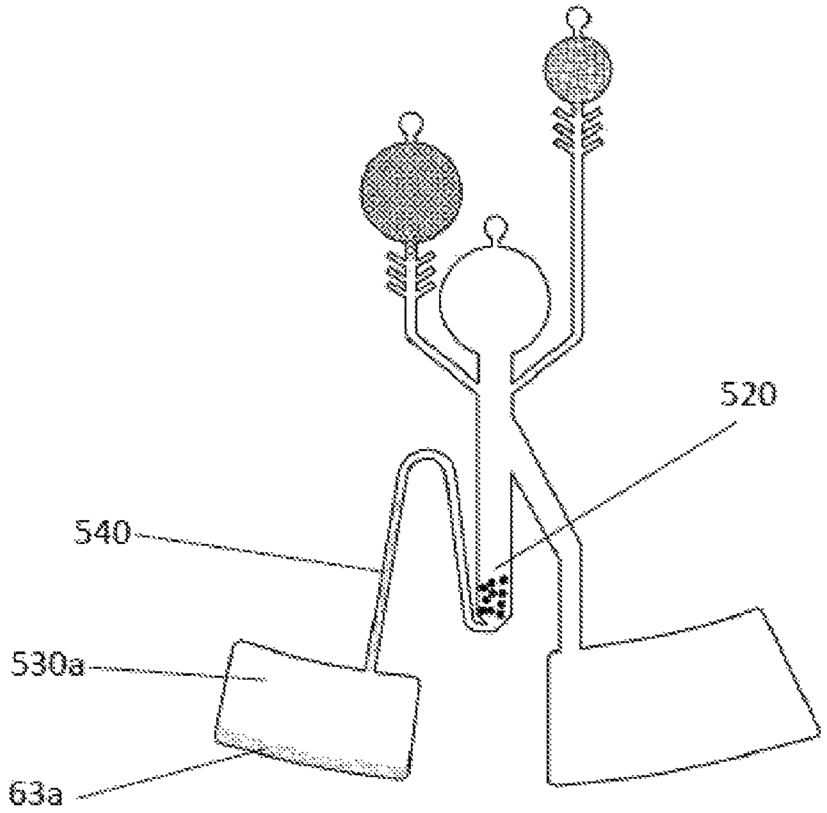

The first rotational speed, which is less than the critical rotational speed ω, is maintained for 30 minutes. As such, the stationary phase 61 and the flowing phase 63*a* may be fully mixed and bonded. The flowing phase 63*a* may fill up with the capillary 540. After the reaction is completed, the rotational speed may be adjusted to the second rotational speed, i.e., 1000 RPM, to generate the syphon effect on the flowing phase 63*a* of the capillary 540 by the gravity force simulated by the centrifugal force. As shown in FIG. 8D, the flowing phase 63*a* in the mixing chamber 520 may be completely drained to the waste chamber 530*a*.

Figure 8E:
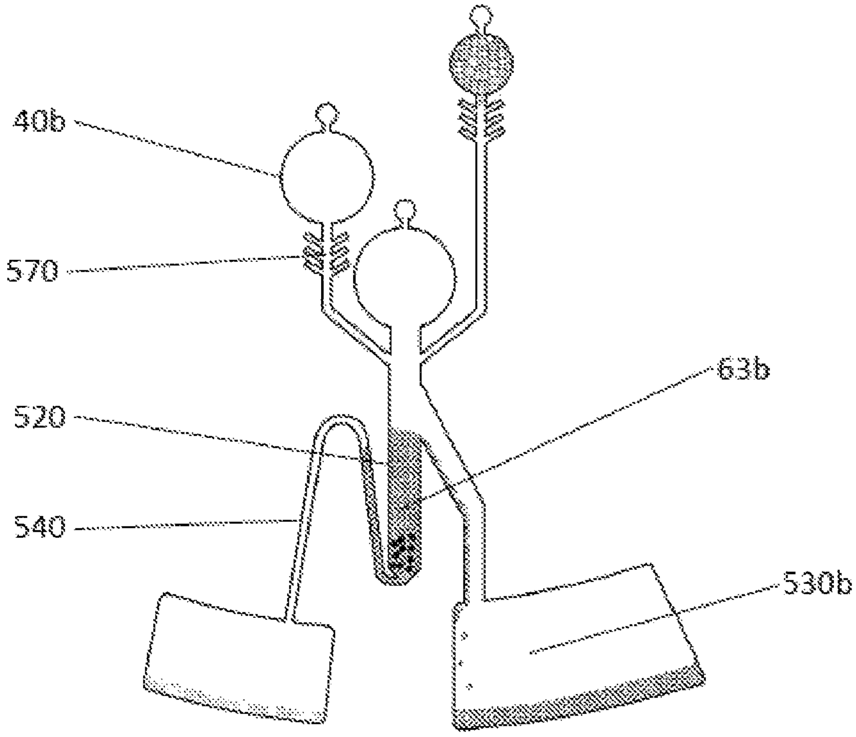

As shown in FIG. 8E, after the flowing phase 63*a* in the mixing chamber 520 is completely drained, the microfluidic disc 20 may be accelerated to an another second rotational speed, i.e., 2000 RPM, and the flowing phase 63*b* in the injection chamber 40*b* may flow through the microfluidic valve 570 and flow into the mixing chamber 520. As shown in FIG. 8A, when the mixing chamber 520 is fully filled up, the overflow channel 550 is configured to perform a quantification process on the flowing phase 63*b*, i.e., the wash buffer. A remaining flowing phase 63*b* may flow into a waste chamber 530*b*. In another example, the waste chamber 530*a* and the waste chamber 530*b* may be a connected structure, and the present disclosure is not limited thereto.

Figure 8F:
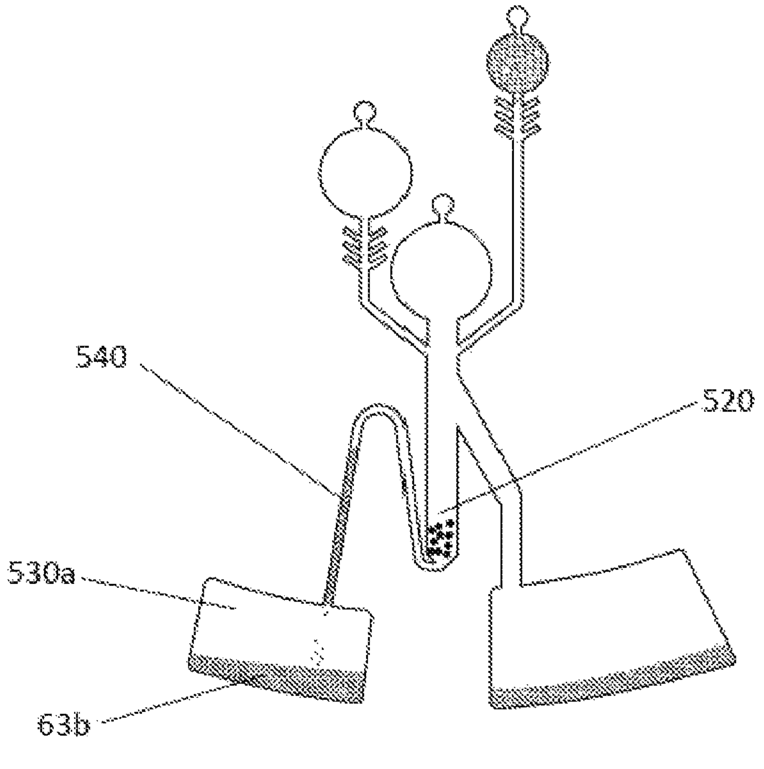

After the flowing phase 63*b* is quantified, the drive module maintains the first rotational speed, Such that the capillary 540 may be filled up with the flowing phase 63*b* by the capillary force. After cleaning the mixing chamber 520, the rotational speed may be accelerated to the second rotational speed, i.e., 1000 RPM, again. As shown in FIG. 8F, the flowing phase 63*b* may be completely drained to the waste chamber 530*a*.

Figure 8G:
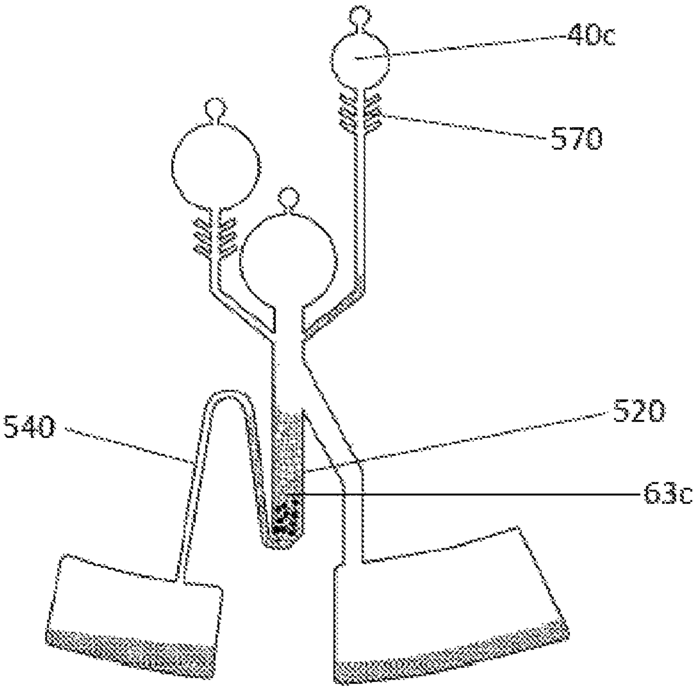

After the flowing phase 63*b* is completely drained to the waste chamber 530*a*, the drive module may accelerate the rotational speed to a highest second rotational speed, i.e., 3000 RPM. As shown in FIG. 8G, the flowing phase 63*c* in the injection chamber 40*c* may flow through the microfluidic valve 570 and flow into the mixing chamber 520. After 15 minutes of reaction, due to the flowing phase 63*c* is the color development reagent, the detection module 30 may detect the reaction results.

The above description is merely the embodiments in the present disclosure, the claim is not limited to the description thereby. The equivalent structure or changing of the process of the content of the description and the figures, or to implement to other technical field directly or indirectly should be included in the claim. All other embodiments obtained by a person of ordinary skill in the art based on the embodiments of the present disclosure without creative efforts shall fall within the protection scope of the present disclosure.

What is claimed is:

1. A microfluidic-based analyzer, comprising:
a drive module;
a microfluidic disc detachably configured on the drive module, wherein the microfluidic disc comprises:
at least one injection chamber;
at least one microfluidic structure connecting to the at least one injection chamber, comprising:
a mixing chamber connecting to the at least one injection chamber;
a capillary connecting to the mixing chamber; and
a waste chamber connecting to the capillary;
wherein the capillary comprises:
a first access connected to the mixing chamber, wherein the first access is configured on a first radius;
a second access connected to the waste chamber, wherein the second access is configured on a second radius; and
a turning section connected to the first access and the second access, wherein the turning section is configured on a third radius:
wherein the first radius is less than the second radius, and the third radius is less than the first radius.

2. The microfluidic-based analyzer as claimed in claim 1, wherein the microfluidic structure comprises an overflow channel comprising:
a third access connected to the mixing chamber, wherein the third access is configured on a fourth radius; and
a fourth access connected to the waste chamber, wherein the fourth access is configured on the second radius;
wherein the fourth radius is less than the first radius.

3. The microfluidic-based analyzer as claimed in claim 2, wherein the third radius is less than the fourth radius.

4. The microfluidic-based analyzer as claimed in claim 1, wherein the mixing chamber comprises at least one magnetic bead.

5. The microfluidic-based analyzer as claimed in claim 1, wherein each of the microfluidic structures further comprises at least one microfluidic valve, and each of the microfluidic valves respectively connects to each of the injection chambers and mixing chambers.

6. The microfluidic-based analyzer as claimed in claim 5, wherein the microfluidic disc comprises a plurality of the microfluidic structures.

7. A microfluidic controlling method of a microfluidic-based analyzer, comprising:
providing the microfluidic-based analyzer as claimed in claim 1;
injecting a liquid into the microfluidic structure;
operating the drive module at a high rotational speed to control the liquid to flow into the mixing chamber, wherein a rotational speed of the drive module comprises a critical rotational speed, a first rotational speed, and a second rotational speed, the first rotational speed is less than the critical rotational speed, and the second rotational speed is greater than the critical rotational speed;
operating the drive module at a low rotational speed, wherein the drive module rotates at the first rotational speed and controls the liquid to flow into the second access by a capillary phenomenon; and
operating the drive module at the high rotational speed, wherein the drive module rotates at the second rotational speed, the drive module controls the liquid to penetrate the second access and to enter the waste chamber until the liquid in the mixing chamber is completely drained.

8. The microfluidic controlling method of the microfluidic-based analyzer as claimed in claim 7, wherein the liquid comprises a stationary phase and a flowing phase.

9. The microfluidic controlling method of the microfluidic-based analyzer as claimed in claim 7, wherein the critical rotational speed is:

$$\omega_c = 60\left(\frac{\gamma\sin\theta}{\pi^2 d_H \rho \Delta R \overline{R}}\right)^{0.5}.$$

* * * * *